(12) United States Patent
Laurent et al.

(10) Patent No.: US 7,446,321 B2
(45) Date of Patent: *Nov. 4, 2008

(54) DIFFERENTIAL WAVELENGTH PHOTOLUMINESCENCE FOR NON-CONTACT MEASURING OF CONTAMINANTS AND DEFECTS LOCATED BELOW THE SURFACE OF A WAFER OR OTHER WORKPIECE

(75) Inventors: Nicolas Laurent, Corenc (FR); Andrzej Buczkowski, Bend, OR (US); Steven G. Hummel, Bend, OR (US); Tom Walker, Portland, OR (US); Amit Shachaf, Palo Alto, CA (US)

(73) Assignee: Nanometrics Incorporated, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/427,080

(22) Filed: Jun. 28, 2006

(65) Prior Publication Data

US 2007/0007466 A1    Jan. 11, 2007

Related U.S. Application Data

(60) Provisional application No. 60/697,055, filed on Jul. 6, 2005.

(51) Int. Cl.
 *G01N 21/64* (2006.01)
 *G01J 1/58* (2006.01)
(52) U.S. Cl. .................................. 250/458.1; 250/459.1
(58) Field of Classification Search .............. 250/458.1, 250/459.1
See application file for complete search history.

(56) References Cited

U.S. PATENT DOCUMENTS 4,246,793 A    1/1981    Fairand et al.

(Continued)

FOREIGN PATENT DOCUMENTS

JP    11-274257    10/1999

(Continued)

OTHER PUBLICATIONS

Montangero, P. et al., "Optical-beam-induced current and photoluminescence techniques for localization of crystallographic defects in optoelectronic devices", Materials Science and Engineering, B24, May 1994, 175-179, 5 pgs.

(Continued)

*Primary Examiner*—Davd P Porta
*Assistant Examiner*—Mindy Vu
(74) *Attorney, Agent, or Firm*—Silicon Valley Patent Group LLP; Michael J. Halbert (57) ABSTRACT

A method for using photoluminescence to identify defects in a sub-surface region of a sample includes performing a first probe of the sample. A first data set, based on the first probe, is produced indicating defects located primarily in a surface layer of the sample. A second data set, based on a second probe, is produced indicating defects located in both the surface layer and a sub-surface region of the sample. The first data set is subtracted from the second data set to produce a third data set indicating defects located primarily in the sub-surface region of the sample. The first data set may optionally be normalized relative to the second data set before performing the subtraction. The first and second probes may advantageously be performed using a first laser and a second laser, respectively, having different wavelengths from each other.

26 Claims, 2 Drawing Sheets

U.S. PATENT DOCUMENTS

| | | | |
|---|---|---|---|
| 4,511,800 | A | 4/1985 | Harbeke et al. |
| 4,740,694 | A | 4/1988 | Nishimura et al. |
| 4,978,862 | A | 12/1990 | Silva et al. |
| 5,202,744 | A | 4/1993 | Louis |
| 5,539,514 | A | 7/1996 | Shishido et al. |
| 5,659,187 | A | 8/1997 | Legoues et al. |
| 5,995,217 | A | 11/1999 | Watanabe |
| 6,075,592 | A | 6/2000 | Banerjee et al. |
| 6,108,079 | A | 8/2000 | Maeshima et al. |
| 6,160,615 | A | 12/2000 | Matsui et al. |
| 6,214,560 | B1 | 4/2001 | Yguerabide et al. |
| 6,256,092 | B1 | 7/2001 | Tomita et al. |
| 6,429,968 | B1 | 8/2002 | Carver |
| 6,462,817 | B1 | 10/2002 | Strocchia-Rivera |
| 6,628,111 | B2 | 9/2003 | Shapiro et al. |
| 6,893,936 | B1 | 5/2005 | Chen et al. |
| 6,911,347 | B2 | 6/2005 | Higgs |
| 7,113,276 | B1 * | 9/2006 | Higgs et al. ................. 356/318 |
| 7,139,083 | B2 | 11/2006 | Fielden et al. |
| 7,245,696 | B2 | 7/2007 | Yun et al. |
| 7,306,951 | B1 | 12/2007 | Benson et al. |
| 2002/0088952 | A1 | 7/2002 | Rao et al. |
| 2002/0119485 | A1 | 8/2002 | Morgan |
| 2003/0061212 | A1 | 3/2003 | Smith et al. |
| 2003/0094579 | A1 | 5/2003 | Hasegawa et al. |
| 2004/0092042 | A1 | 5/2004 | Higgs |
| 2004/0252297 | A1 * | 12/2004 | Fairley et al. ............. 356/237.5 |
| 2006/0262296 | A1 | 11/2006 | Higgs |
| 2006/0281281 | A1 | 12/2006 | Tanzawa et al. |
| 2007/0000434 | A1 | 1/2007 | Buczkowski |
| 2007/0008518 | A1 * | 1/2007 | Hummel et al. .......... 356/237.1 |
| 2007/0008526 | A1 | 1/2007 | Buczkowski |
| 2007/0176119 | A1 | 8/2007 | Hummel |

FOREIGN PATENT DOCUMENTS

| | | |
|---|---|---|
| JP | 11-354599 | 12/1999 |
| JP | 2000-193597 A | 7/2000 |
| JP | 2003-045928 A | 2/2003 |
| WO | WO-98/11425 A1 | 3/1998 |
| WO | WO-02/29883 A1 | 4/2002 |
| WO | WO-02/077621 A1 | 10/2002 |
| WO | WO-2004/010121 A1 | 1/2004 |
| WO | WO-2004/090516 A1 | 10/2004 |
| WO | WO-2007/005438 A2 | 1/2007 |
| WO | WO-2007/005438 A3 | 1/2007 |
| WO | WO-2007/008311 A2 | 1/2007 |
| WO | WO-2007/008399 A2 | 1/2007 |
| WO | WO-2007/008399 A3 | 1/2007 |
| WO | WO-2007/008430 A2 | 1/2007 |
| WO | WO-2007/008430 A3 | 1/2007 |

OTHER PUBLICATIONS

Pritchard, R. E. et al., "Composition assessment by spatially resolved photoluminescence of InGaAs and InGaAsP epilayers grown on recessed InP substrates", Semiconductor Science and Technology, Jun. 8, 1993, 1166-1172, No. 6, Bristol, GB, 7 pgs.

Bajaj, J. et al., "Spatially resolved characterization of HgCdTe materials and devices by scanning laser microscopy", Semiconductor Science and Technology, Jun. 8, 1993, 872-887, No. 6S, Bristol, GB, 16 pgs.

Ribes, A. C. et al., "Photoluminescence imaging of porous silicon using a confocal scanning laser macroscope/microscope", Applied Physics Letters, 66 May 1, 1995, 2321-2323, No. 18, Woodbury, NY, US, 3 pgs.

Moore, C. J. L. et al., "A Spatially resolved spectrally resolved photoluminescence mapping system", Journal of Crystal Growth, 103 Jun. 1990 II, Nos. 1/4, 21-27, Elsevier Science Publishers, North-Holland, 7 pgs.

Tajima, Michio, "Characterization of semiconductors by photoluminescence mapping at room temperature", Journal of Crystal Growth, 130 (1990), 1-7, , Elsevier Science Publishers, North-Holland, 7 pgs.

Miner, C. J., "Non-destructive, whole wafer assessment of optoelectronic epitaxial materials", Semiconductor Science and Technology, 7 (1992), A10-A15, IOP Publishing Ltd, 6 pgs.

Distefano, T. H. et al., "Non-Destructive, Non-Contacting Test of Si Wafers by Thermore-Flectance", IBM Technical Disclosure Bulletin, Feb. 1987, 10 pgs.

RPM2000 Rapid Photoluminescence Mapper, Sales Brochure, date unknown, 6 pages.

SPHER The key to revealing hidden problems in Si wafers, Sales Brochure, date unknown, 8 pages.

Bellone, S. et al. (1991). "Recombination measurement of n-type heavily doped layer in high-low silicon junctions," *IEEE Trans. Electron. Devices* 38(3):532-537.

Commere, B. et al. (Sep. 1988). "Control of the fabrication steps of InP MIS transistors by means of scanning photoluminescence measurements," *Journal de Physique*, Colloque, Paris, France 49(C-4)(Suppl. 9): 431-436.

Derbyshire, K. (Summer 2004). "The engineered substrate's balancing act: performance gains versus greater costs and increased yield risks," *Yield Management Solutions Magazine* located at http://www.kla-tencor.com/company/magazine/summer04/coverstory. pdf, pp. 29.

Fitzgerald, E.A. et al. (Nov. 3, 1998). "Dislocations in relaxed SiGe/Si heterostructures," MIT Department of Materials Science and Engineering and AmberWave Technologies, pp. 227-238.

Higgs, V et al. (Feb. 15, 1993). "Characterization of compositionally graed Si1-xGex alloy layers by photoluminescence spectroscopy and by cathodoluminescence spectroscopy and imaging," *Journal of Applied Physics* 73(4):152-156.

Higgs, V. (2000). Characterization of Si, SiGe, and SOI structures using photoluminescence, *Materials Research Society Symposium Proceedings* 588:129-140.

Higgs, V. et al. (Sep. 13, 1999). "Application of room temperature photoluminescence for the characterization of impurities and defects in silicon," *Proceedings of SPIE* 3895:21-37.

Korsunska, N.E. et al. (Jul. 2004). "High temperature photoluminescence spectroscopy in p-type SiC," *Semiconductor Science and Technology* 19(7):833-838.

Ressel, P. et al. (1993). "Optimized proton implantation step for vertical-cavity surface-emitting lasers," *Electron. Lett.* 29(10):918-919.

Tajima, M. et al. (1990). "Mapping of microdefects in silicon crystals by photoluminescence at room temperature," *Semiconductor Silicon 1990* from Proceedings of the Sixth International Symposium on Silicon Materials Science and Technology, eds. H. R. Huff et al., Electrochem. Soc., Inc.: Pennington, NJ, pp. 994-1004.

Titus, J. (Jun. 1, 2004). "Keep an eye on wafer defects," *Test & Measurement World* located at http://www.reed-electronics.com/tmworld/article/CA420488.html, 5 pages.

Westrate, S. et al. (Feb. 2002). "Photoluminescence mapping detects CU contamination in SI wafers," *Solid State Technology* 45(2):57-58.

Office Action mailed on Jan. 5, 2000 for U.S. Appl. No. 09/254,521, filed Mar. 8, 1999 by Higgs et al., 6 pages.

Response to Office Action mailed on Sep. 19, 2005 for U.S. Appl. No. 09/254,521, filed Mar. 8, 1999 by Higgs et al., 14 pages.

Notice of Allowance mailed on May 18, 2006 for U.S. Appl. No. 09/254,521, filed Mar. 8, 1999 by Higgs et al., 14 pages.

Ex Parte Quayle Action mailed on Dec. 11, 2007 for U.S. Appl. No. 11/528,723, filed Sep. 26, 2006 by Higgs et al., 7 pages.

Restriction Requirement mailed on Jun. 14, 2007 for U.S. Appl. No. 11/177,735, filed Jul. 8, 2005 by Buczkowski, 6 pages.

Response to Restriction Requirement mailed on Jul. 23, 2007 for U.S. Appl. No. 11/177,735, filed Jul. 8, 2005 by Buczkowski, 16 pages.

Office Action mailed on Sep. 12, 2007 for U.S. Appl. No. 11/177,735, filed Jul. 8, 2005 by Buczkowski, 42 pages.

Office Action mailed on Oct. 3, 2007 for U.S. Appl. No. 11/426,877, filed Jun. 27, 2006 by Hummel et al., 8 pages.

Response to Office Action mailed on Dec. 20, 2007 for U.S. Appl. No. 11/426,877, filed Jun. 27, 2006 by Hummel et al., 10 pages.

International Search Report mailed on Dec. 18, 1997 for PCT Application No. PCT/GB97/02388 filed on Sep. 5, 1997 by Bio-Rad Micromeasurements, Ltd, 2 pages.

International Search Report mailed on Aug. 31, 2007 for PCT Application No. PCT/US06/25083 filed on Jun. 27, 2006 by Accent Optical Technologies, Inc., 4 pages.

International Search Report mailed on Oct. 1, 2007 for PCT Application No. PCT/US06/24938 filed on Jun. 27, 2006 by Accent Optical Technologies, Inc., 4 pages.

International Search Report mailed on Sep. 4, 2007 for PCT Application No. PCT/US06/25257 filed on Jun. 28, 2006 by Nanometrics, Inc., 2 pages.

International Search Report mailed on Jul. 22, 2004 for PCT Application No. PCT/GB2004/001521 filed on Apr. 8, 2004 by AOTI Operating, Inc., 4 pages.

Notice of Allowance mailed by Examiner Djura Malevic on Aug. 8, 2008, for U.S. Appl. No. 11/426,877 filed on Jun. 27, 2006 by Hummel et al., 7 pages.

Request for Continued Examination mailed on Sep. 4, 2008, for U.S. Appl. No. 11/426,877 filed on Jun. 27, 2006 by Hummel et al., 4 pages.

Ivanov, I.G. et al., "Donor doping calibration in 4H-SiC using photoluminescence spectroscopy", IEEE 1996, 0-7803-3179-6/96 pp. 223-226.

Response to Office Action with RCE and Amendment filed Jan. 30, 2008 for U.S. Appl. No. 11/528,723 filed on Sep. 26, 2006 by Higgs et al. 15 pages.

Notice of Allowance mailed by Examiner Michelle R. Connelly Cushwa on May 1, 2008 for U.S. Appl. No. 11/528,723 filed on Sep. 26, 2006 by Higgs et al., 7 pages.

RCE and IDS mailed on Jul. 24, 2008 for U.S. Appl. No. 11/528,723 filed on Sep. 26, 2006 by Higgs et al., 4 pages.

Notice of Allowance mailed by Examiner Michelle R. Connelly Cushwa on Aug. 18, 2008 by Examiner Michelle R. Connelly Cushwa for U.S. Appl. No. 11/528,723 filed on Sep. 26, 2006 by Higgs et al., 7 pages.

RCE and IDS mailed on Aug. 27, 2008 for U.S. Appl. No. 11/528,723 filed on Sep. 26, 2006 by Higgs et al., 5 pages.

Response to Office Action dated Feb. 12, 2008 for U.S. Appl. No. 11/177,735 filed on Jul. 8, 2005 by Buczkowski, 22 pages.

Office Action mailed by Examiner Rebecca Slomski on Jun. 23, 2008, for U.S. Appl. No. 11/177,735 filed on Jul. 8, 2005 by Buczkowski, 33 pages.

Office Action mailed by Examiner David S. Baker on Jun. 2, 2008, for U.S. Appl. No. 11/343,500, filed on Jan. 30, 2006 by Hummel (32 pgs).

Office Action mailed by Examiner Isiako O. Akanbi on May 27, 2008, for U.S. Appl. No. 10/549,865, filed on Jul. 28, 2006 by Higgs, 19 pgs.

Response to Office Action dated Aug. 27, 2008 for U.S. Appl. No. 10/549,865, filed on Jul. 28, 2006 by Higgs, 10 pgs.

\* cited by examiner

DIFFERENTIAL WAVELENGTH PHOTOLUMINESCENCE FOR NON-CONTACT MEASURING OF CONTAMINANTS AND DEFECTS LOCATED BELOW THE SURFACE OF A WAFER OR OTHER WORKPIECE

PRIORITY CLAIM

This application claims the benefit of U.S. Provisional Application No. 60/697,055, filed Jul. 6, 2005, which is incorporated herein by reference.

BACKGROUND

Photoluminescence imaging or photoluminescence spectroscopy is a contactless, nondestructive method of probing the electronic structure of materials, such as silicon semiconductor wafers, as well as other workpieces and materials. In a typical photoluminescence process, light is directed onto a wafer or other workpiece or sample (hereinafter collectively referred to as a "wafer"), where some of the light is absorbed. The absorbed light imparts excess energy into the material via a process of "photo-excitation." This excess energy is dissipated by the wafer through the emission of light, or photoluminescence. The intensity and spectral content of this photoluminescence is directly related to various material properties of the wafer.

Photoluminescence imaging processes may be used to identify and quantify defects and contaminants present in the wafer based on spatial variations in the photoluminescence images produced. One photoluminescence imaging process, as described in International Application Number PCT/GB97/02388 (publication number WO 98/11425), which is incorporated herein by reference, involves probing the surface and/or the sub-surface bulk region of the wafer with one or more lasers of varying excitation wavelengths. A laser of a given wavelength is directed into the wafer and penetrates the wafer to a given depth. Return light emitted from the wafer is detected and quantified by a detection system. Images of the measured return light, including spatial images of defects and contaminants in the wafer, may then be produced by the detection system or by an associated image-producing system.

While these images may effectively identify defects and contaminants in the wafer, they are sometimes distorted due to non-uniformity in the surface layer or epitaxial layer of the wafer. Wafer surface variances may be caused by, for example, a Bernoulli wand or similar device that suspends the wafer and applies moving gas over the wafer's surface. The distorted images resulting from these surface variances can make it difficult or impossible to accurately identify and quantify defects and contaminants in the sub-surface or bulk region of the wafer. Thus, to obtain a more accurate measurement of the defects and contaminants in the bulk region of a wafer, photoluminescence image distortion, caused by variances in the surface layer of the wafer, must be substantially reduced or eliminated.

SUMMARY

A method and apparatus uses photoluminescence to identify defects in a sub-surface region of a sample. A first data set is produced indicating defects located primarily in a surface layer of the sample. A second data set is produced indicating defects located in the surface layer and in a sub-surface region of the sample. The first data set is then subtracted from the second data set to produce a third data set indicating defects located primarily in the sub-surface region of the sample. The first data set may optionally be normalized relative to the second data set before the subtracting step is performed.

The first and second data sets may be advantageously generated by performing first and second probes, using first and second lasers, respectively. The second laser may have a wavelength greater than that of the first laser, or the first laser may have a wavelength greater than that of the second laser.

Other features and advantages of the invention will appear hereinafter. The features of the invention described above can be used separately or together, or in various combinations of one or more of them. The invention resides as well in sub-combinations of the features described. Furthermore, many of the method steps described herein may be performed in a different order than that which is explicitly described.

BRIEF DESCRIPTION OF THE DRAWINGS

In the drawings, wherein the same reference number indicates the same element in each of the figures.

DETAILED DESCRIPTION OF THE DRAWINGS

Various embodiments of the invention will now be described. The following description provides specific details for a thorough understanding of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Any terminology intended to be interpreted in any restricted manner will be overtly and specifically defined as such in this detailed description section.

Figure 1:
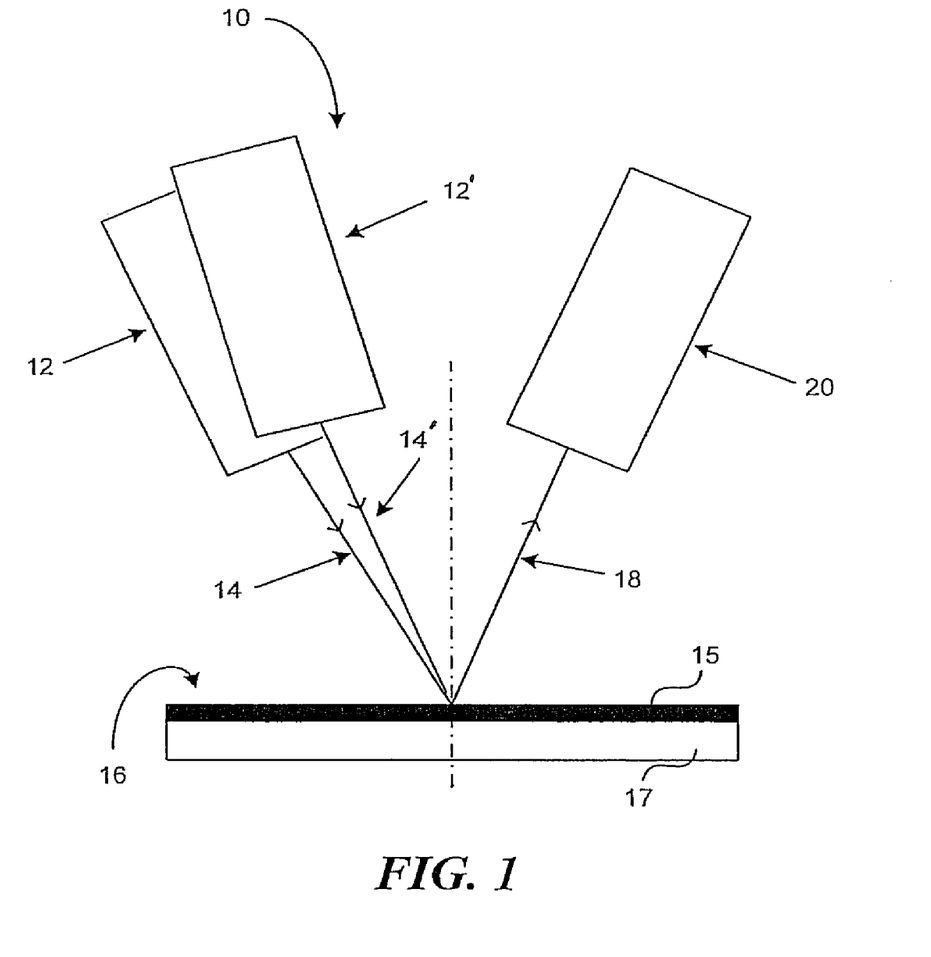
FIG. 1 is a schematic diagram illustrating one configuration of the basic components of a photoluminescence imaging system.

FIG. 1 schematically illustrates the basic components of one configuration of a photoluminescence spectroscopy or imaging system 10. The photoluminescence imaging system 10 includes a light source 12, such as a laser diode or other suitable light-emitting diode (LED) or device. The light source 12 generates an illumination or incident laser beam 14 or other light beam (e.g., a UV light beam) toward, either directly or via reflection off of one or more optical components, a wafer 16 or other sample. The term "wafer," as used herein, includes any sample upon which photoluminescence imaging may be performed. The term "laser beam," as used herein, includes any light beam suitable for exciting one or more material layers in the wafer.

The wafer 16 may be a silicon semiconductor wafer or other microelectronic, microelectro-mechanical, or optoelectronic substrate or other sample. The wafer 16 may include one or more epitaxial layers or other surface layers 15 grown on, applied on, or otherwise located on a substrate region or other bulk region 17 of the wafer 16. For example, the wafer 16 may include a bulk region 17 of silicon (Si) and a surface layer 15 of silicon germanium (SiGe). The wafer 16 may include any number of layers including any number of materials and/or compositions.

The incident laser beam 14 penetrates the wafer 16 to a given depth, which is substantially a function of the wavelength of the incident laser beam 14. At least a portion of the incident laser beam 14 is absorbed by the wafer 16, and return light 18 emitted from the wafer 16 (corresponding to the absorbed incident laser beam 14) is then detected by a detector 20, such as a CCD array or other suitable detection system. A microprocessor, computer, or other processing system is preferably included in, or is connected to or otherwise associated with, the detector 20 for processing data from the return light 18 detected by the detector 20.

Figure 2:
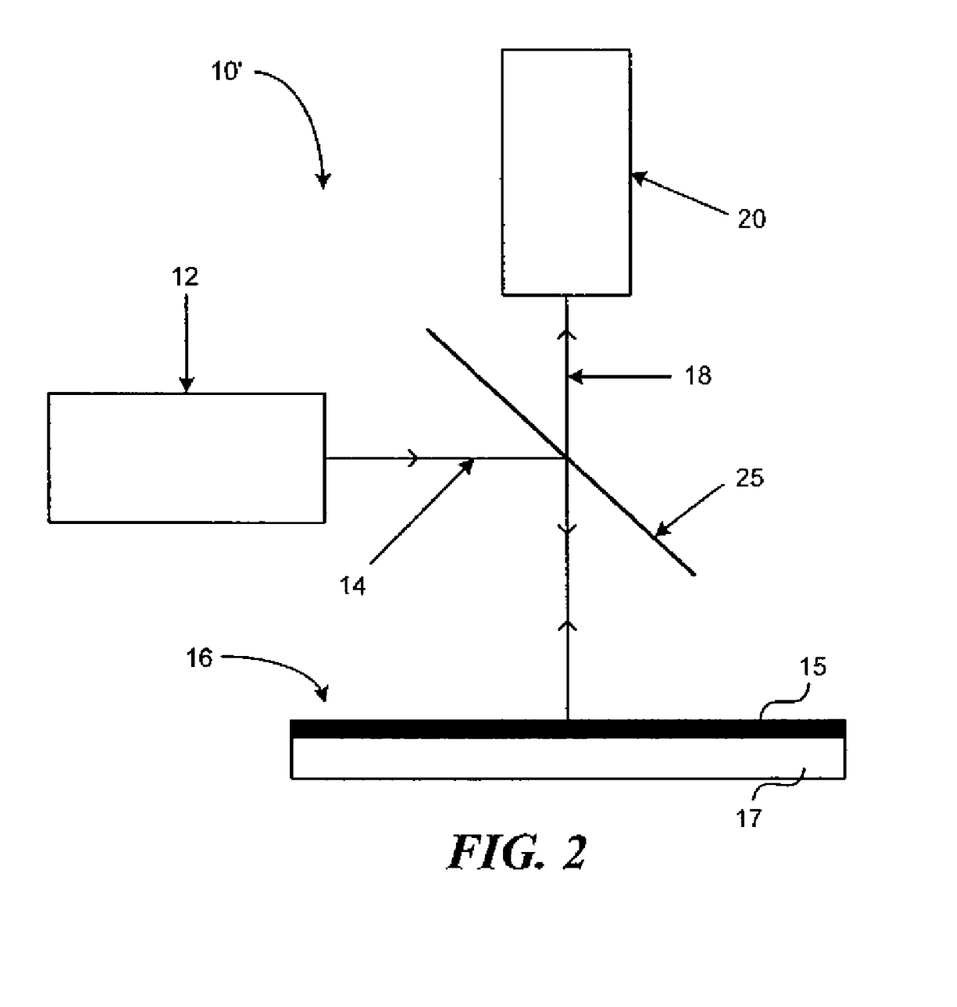
FIG. 2 is a schematic diagram illustrating another configuration of the basic components of a photoluminescence imaging system.

FIG. 2 illustrates an alternative configuration of a photoluminescence imaging system 10' including a beam splitter 25 for reflecting the incident laser beam 14 toward the wafer 16, and for transmitting the return light 18 toward the detector 20. One or more additional beam splitters 25 or other optical elements or mirrors may be included in the photoluminescence imaging system 10 or 10' to achieve a desired size or configuration of the system, and/or to select, focus, collect, and/or direct the incident laser beam 14 and/or the emitted return light throughout the system.

The photoluminescence imaging system 10 or 10' may further include any number of additional or alternative components for performing photoluminescent imaging or spectroscopy on a wafer 16. For example, the photoluminescence imaging system 10 may include an imaging microscope having multiple laser sources, a display screen for visually displaying photoluminescent image data, a wafer holder for supporting the wafer 16, one or more filters for filtering incident or return light, as well as any other suitable components.

A detailed example of a photoluminescent imaging system is described in International Application Number PCT/GB97/02388. For ease of description, reference character "10" will be used throughout the remainder of this description to identify a suitable photoluminescence imaging system. It is to be understood however, that any system configuration, such as the system 10' illustrated in FIG. 2, or the detailed system described in International Application Number PCT/GB97/02388, may be used to perform the photoluminescence imaging processes described below.

Images of the sub-surface or bulk region of a wafer, which are produced using a photoluminescence imaging process, are often distorted or obscured as a result of surface layer variances in the wafer Methods of substantially reducing or eliminating this distortion, so that defects in the bulk or sub-surface region of the wafer can be readily identified and quantified, will now be described. The term "defects," as used herein, includes any contaminants, flaws, discontinuities, impurities, variations, and/or other non-uniformities of a metric associated with a state of the wafer.

The wafer 16 is first loaded into a photoluminescence imaging system 10 and secured to a wafer holder or other support. Depending on the system configuration, one or more wafers 16 may be loaded into the photoluminescence imaging system 10 for processing. For ease of description, the process of imaging a single wafer 16 will be described herein. A first laser 12, having a first wavelength, is directed toward a wafer 16. The wavelength of the first laser 12 is preferably chosen such that the first laser beam 14 penetrates the wafer 16 to a depth substantially equal to, or slightly greater than, the thickness of the surface layer 15 or epitaxial layer of the wafer 16. For example, a green laser, having a wavelength of approximately 532 nm, may be used to penetrate the surface layer 15 of a typical silicon semiconductor wafer. This process of penetrating the surface layer 15 with a first laser, while not penetrating a substantial portion of the bulk or sub-surface region 17 of the wafer 16, is referred to herein as a surface probe.

Return light from the surface probe is detected by the detector 20, and is processed by a microprocessor or similar device to produce intensity values or defect data corresponding to defects located primarily in the surface layer region 15 of the wafer 16. The term "primarily," as used herein, means predominantly or entirely. This surface layer defect data may optionally be converted into a visual image indicating the locations and quantity of defects in the surface layer of the wafer 16. The visual image may be displayed on a monitor or other suitable display screen and/or may be printed out in hard copy form via a printer or similar device. The surface layer defect data may then be stored or otherwise preserved for later use.

Once the surface probe is completed, a second laser 12', having a second wavelength, is directed toward the wafer 16. The wavelength of the second laser is preferably chosen such that the second laser beam 14' penetrates the wafer 16 to a depth substantially equal to the total thickness of the wafer 16. For example, a red laser, having a wavelength of approximately 827 nm, may be used to penetrate at least substantially through the bulk region 17 of a typical silicon semiconductor wafer. As a result, this bulk probe or sub-surface probe yields defect data corresponding to both the surface layer 15 and the bulk or sub-surface region 17 of the wafer 16.

The wavelength of the second laser may of course be chosen such that the second laser does not penetrate all the way through the bulk region 17 of the wafer 16, or so that it does not penetrate beyond a given depth in the wafer 16. This may be done in situations, for example, where defect measurements are not desired or required below a given depth within the bulk region 17 of the wafer 16.

In general, the first and second lasers may be of any suitable wavelengths to penetrate the wafer 16 to desired depths. If the surface layer 15 of a given wafer 16 is thicker than the depth to which a 532 nm (green) laser will penetrate, for example, then a laser having a greater wavelength than 532 nm may be used to penetrate through the entire surface layer 15 (or through substantially all of the surface layer 15). The first and second lasers, therefore, may be of any wavelengths suitable for penetrating the wafer to depths required for a given application. Moreover, in alternative embodiments, the bulk probe may be performed prior to performing the surface probe, or the bulk probe and the surface probe may be concurrently performed.

Return light from the bulk probe is detected by the detector 20, and is processed by the microprocessor or other device to produce intensity values or defect data corresponding to defects in both the bulk region 17 and the surface layer region 15 of the wafer 16. This defect data may optionally be converted into a visual image indicating the locations and quantity of defects in both the bulk region 17 and the surface layer 15 of the wafer 16. The visual image may be displayed on a monitor or other suitable display screen and/or may be printed out in hard copy form via a printer or similar device. As explained above, however, such an image may be distorted or obscured due to variations in the surface layer 15 of the wafer 16. Thus, the image may not effectively convey the locations and/or quantity of defects present in the wafer 16, particularly in the bulk region of the wafer 16.

In one embodiment, once the results of the surface probe and the bulk probe have been obtained, the intensity values or defect data points obtained from the surface probe are mathematically subtracted from the intensity values or defect data points obtained from the bulk probe. Put another way, intensity values or defect data points common to both the surface probe and the bulk probe (i.e., intensity values or defect data points corresponding to defects primarily in the surface layer 15 of the wafer 16) are mathematically removed from the bulk probe data to produce a new data set. This subtraction or removal process may be performed via a software program, or any other suitable program or processor, that compares the data points from the surface probe and the bulk probe and subtracts off or otherwise removes the data points common to both probes.

By removing the defect data corresponding to the uneven surface layer 15, the new data set, which corresponds primarily to defects in the bulk region 17 of the wafer 16, is no longer distorted by the previously overlying surface layer defect data. Accordingly, a substantially clearer image of the location and concentration of defects present in the bulk region 17 of the wafer 16 may be produced using the new data set. A visual image of these bulk region defects may be generated using an image-producing device associated with, or located in, the detector 20 and/or with other system elements. The visual image may be displayed on a monitor or other suitable display screen and/or may be printed out in hard copy form via a printer or similar device.

In another embodiment, the surface probe data and the bulk probe data are normalized relative to each other, before the subtraction process is performed, to enhance the defect images and to make them more easily mathematically processable. The normalization process may include adjusting the contrast and/or the brightness of one or both of the images produced by the surface and bulk probes so that they have the same, or substantially the same, relative intensity. Such a normalization process may be performed by a software program or other suitable program or processor, which may be the same as or different than the program or processor that performs the subtraction process.

The normalization process may alternatively or additionally include plotting data points from the surface probe versus data points from the bulk probe and removing any mathematically outlying data points, thus yielding images that are more readily mathematically processable. For example, a software program or other suitable program or processor, which may be the same as or different than the program or processor that performs the subtraction process, may curve-fit lines to their respective data points and then remove any outlying data points located beyond a predetermined tolerance limit or distance from the lines.

By normalizing the surface probe data relative to the bulk probe data before performing the subtraction process, a clearer, more precise new data set, corresponding to defect data located primarily in the bulk region 17 of the wafer 16, may be obtained. Any other suitable method(s) for normalizing the bulk probe and surface probe data and/or corresponding images relative to each other may additionally or alternatively be used.

The photoluminescence imaging processes described above may also be performed on wafers having more than two layers. In such a case, the same or a similar process may be performed wherein a first laser having a first wavelength is penetrated to a first depth located approximately at an upper region of a layer to be measured, and a second laser having a second wavelength is penetrated to a second depth located approximately at a lower region of the layer to be measured. The normalization and subtraction processes (subtracting the first measurement from the second measurement, in this example) described above may then be applied to generate defect data corresponding to the desired layer.

The photoluminescence imaging processes described above may be performed at approximately room temperature, as described in International Application Number PCT/GB97/02388. Alternatively, any of the photoluminescence imaging processes may be performed at higher or lower temperatures, including significantly higher or lower temperatures, depending upon the needs of a given application.

Any suitable devices and components may be used to perform the photoluminescence processes described herein. For example, various means may be used to produce lasers of varying excitation wavelengths, such as one or more laser diodes or LEDs or other suitable light-producing devices. Any suitable means for detecting return light emitted from a wafer may also be used, such as a CCD array, a spectrometer, or any other suitable detecting system or device. Means for generating defect data based on the detected return light may include a software program or other program or processor, which may be included in or associated with the detector and/or with other elements in the photoluminescence imaging system. Such a program or processor may also be a means for performing the subtracting and/or optional normalizing processes described above. Alternatively, one or more separate programs or processors may be used to perform one or more of these processes.

Thus, while several embodiments have been shown and described, various changes and substitutions may of course be made, without departing from the spirit and scope of the invention. Many of the method steps described herein, for example, may be performed in a different order than that which is specifically described. For example, in any of the embodiments described above, the bulk or sub-surface probe may be performed before the surface probe. The invention, therefore, should not be limited, except by the following claims and their equivalents.

What is claimed is:

1. A method for using photoluminescence, comprising:
producing a first data set characteristic of defects located primarily in a surface layer of a sample;
producing a second data set characteristic of defects located in the surface layer and in a sub-surface region of the sample; and
subtracting the first data set from the second data set to produce a third data set indicating defects located primarily in the sub-surface region of the sample.

2. The method of claim 1 further comprising normalizing the first and second data sets relative to each other before performing the subtraction.

3. The method of claim 2 wherein normalizing comprises adjusting at least one of a contrast and a brightness of at least one of a first and second image corresponding to the first and second data sets, respectively.

4. The method of claim 2 wherein normalizing comprises eliminating outlying data points from at least one of the first and second data sets.

5. The method of claim 1 wherein a first laser used to produce the first data set has a wavelength of approximately 532 nm and a second laser used to produce the second data set has a wavelength of approximately 827 nm.

6. The method of claim 1 further comprising convening the first data set into a first image showing defects in the surface layer of the sample, and converting the second data set into a second image showing defects in the surface layer and in the sub-surface region of the sample, before performing the subtraction.

7. The method of claim 1 further comprising convening the third data set into an image showing defects located primarily in the sub-surface region of the sample.

8. The method of claim 1 wherein producing a first data set comprises performing a first probe of the sample using a first laser having a first wavelength, and wherein producing a second data set comprises performing a second probe of the sample using a second laser having a second wavelength.

9. The method of claim 8 wherein the first and second probes are concurrently performed.

10. The method of claim 1 wherein subtracting comprises removing, from the second data set, data points common to both the first and second data sets to yield the third data set.

11. The method of claim 1 wherein the subtraction is performed by a software program or a processor.

12. A method for identifying defects in a sample, comprising:
directing a first laser to a first depth in the sample;
generating first defect data corresponding to first return light emitted from the sample;
directing a second laser to a second depth, greater than the first depth, in the sample;
generating second defect data corresponding to second return light emitted from the sample; and
subtracting the first defect data from the second defect data to obtain third defect data corresponding to defects in a region of the sample located deeper than the first depth.

13. The method of claim 12 further comprising normalizing the first and second defect data relative to each other before performing the subtraction.

14. The method of claim 13 wherein normalizing comprises adjusting at least one of a contrast and a brightness of at least one of a first and second image corresponding to the first and second defect data, respectively.

15. The method of claim 13 wherein normalizing comprises eliminating outlying data points from at least one of the first and second defect data.

16. The method of claim 12 wherein the first and second lasers are concurrently directed into the sample.

17. A method for using photoluminescence to identify defects in a subsurface region or bulk region of a sample, comprising:
performing a surface probe with a first laser to generate first defect data;
performing a bulk probe with a second laser to generate second defect data;
normalizing the first defect data relative to the second defect data to yield normalized first defect data and normalized second defect data; and
calculating a difference between the normalized second defect data and the normalized first defect data to yield third defect data corresponding to defects located primarily in the bulk region of the sample.

18. The method of claim 17 wherein normalizing comprises modifying one or both of the first and second defect data.

19. The method of claim 17 wherein normalizing comprises adjusting at least one of a contrast and a brightness of one or both of a first and second image corresponding to the first and second defect data, respectively.

20. The method of claim 17 wherein normalizing comprises eliminating outlying data points from at least one of the first and second defect data.

21. The method of claim 20 wherein eliminating outlying data points comprises:
plotting the first defect data versus the second defect data;
curve-fitting first and second lines to the plotted first defect data and second defect data, respectively; and
removing data points located beyond a predetermined tolerance limit or distance from the first and second lines.

22. The method of claim 17 wherein calculating a difference comprises removing, from the second defect data, data points common to both the normalized first and second defect data to yield the third defect data.

23. The method of claim 17 wherein the bulk probe and the surface probe are concurrently performed.

24. A photoluminescence imaging apparatus, comprising:
means for generating first data characteristic of defects located in a first region of a sample;
means for generating second data characteristic of defects located in the first region and in a second region of a sample; and
means for subtracting the first data from the second data to obtain third data characteristic of defects primarily in the second region.

25. The apparatus of claim 24 further comprising means for normalizing the first data relative to the second data.

26. The apparatus of claim 24 further comprising:
means for producing a first laser having a first wavelength to penetrate the sample to a lower depth of the first region;
means for producing a second laser having a second wavelength, which is greater than the first wavelength, to penetrate the sample to a lower depth of the second region; and
means for detecting return light, emitted from the sample, corresponding to the first and second lasers.

* * * * *

UNITED STATES PATENT AND TRADEMARK OFFICE
CERTIFICATE OF CORRECTION

PATENT NO. : 7,446,321 B2
APPLICATION NO. : 11/427080
DATED : November 4, 2008
INVENTOR(S) : Nicolas Laurent Page 1 of 1

It is certified that error appears in the above-identified patent and that said Letters Patent is hereby corrected as shown below:

<u>Claim 6, Line 1</u>

After "further comprising", delete "convening" and substitute --converting--.

<u>Claim 7, Line 1</u>

After "further comprising", delete "convening" and substitute --converting--.

Signed and Sealed this

Twenty-third Day of December, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,446,321 B2 |
| APPLICATION NO. | : 11/427080 |
| DATED | : November 4, 2008 |
| INVENTOR(S) | : Nicolas Laurent |

Page 1 of 1

It is certified that error appears in the above-identified patent and that said Letters Patent is hereby corrected as shown below:

<u>Column 6, Claim 6, Line 62</u>

After "further comprising", delete "convening" and substitute --converting--.

<u>Column 7, Claim 7, Line 1</u>

After "further comprising", delete "convening" and substitute --converting--.

This certificate supersedes the Certificate of Correction issued December 23, 2008.

Signed and Sealed this

Twenty-seventh Day of January, 2009

JOHN DOLL
*Acting Director of the United States Patent and Trademark Office*